United States Patent [19]
Lyons, III et al.

[11] Patent Number: 5,263,967
[45] Date of Patent: Nov. 23, 1993

[54] MEDICAL INSTRUMENT WITH DUAL ACTION DRIVE

[75] Inventors: William G. Lyons, III, Wilbraham; John Kirwan, Middleton, both of Mass.

[73] Assignee: Brimfield Precision Incorporated, Brimfield, Mass.

[21] Appl. No.: 883,080

[22] Filed: May 15, 1992

[51] Int. Cl.$^5$ .................. A61B 17/42; A61B 17/44
[52] U.S. Cl. .................... 606/205; 606/208; 294/115; 294/116
[58] Field of Search ............ 606/120, 151, 157, 158, 606/203, 205, 206, 208; 433/4, 157, 159; 294/115, 116

[56] References Cited
U.S. PATENT DOCUMENTS

| | | | |
|---|---|---|---|
| 4,345,596 | 8/1982 | Young | 128/214 R |
| 4,559,944 | 12/1985 | Jaeger | 128/344 |
| 4,596,249 | 6/1986 | Freda et al. | 128/334 R |
| 4,597,390 | 7/1986 | Mulhollan et al. | 128/340 |
| 4,712,545 | 12/1987 | Konkanen | 128/305 |
| 4,732,149 | 3/1988 | Sutter | 128/303.17 |
| 4,792,330 | 12/1988 | Lazarus et al. | 604/174 |
| 4,865,032 | 9/1989 | Jones | 128/340 |
| 4,872,456 | 10/1989 | Hasson | 128/321 |
| 4,949,717 | 8/1990 | Shaw | 606/147 |
| 5,052,402 | 10/1991 | Bencini et al. | 606/206 |
| 5,170,800 | 12/1992 | Smith et al. | 606/205 |

Primary Examiner—Jerome L. Kruter
Attorney, Agent, or Firm—Weingarten, Schurgin, Gagnebin & Hayes

[57] ABSTRACT

A medical instrument including a tubular extension within which and to which two movable end effectors, such as jaw members, are rotatably attached by a pivot. The proximal end of each end effector is pivotally attached to and butts against a drive surface of its respective arm of a dual action drive member also located within the tubular extension. As the dual action drive member is moved proximally or distally within the tubular extension, the distal ends of the end effectors rotate or counter rotate about the pivot in opposition to one another. The dual action drive member paired arms have end surfaces which transfer, to the end effectors, the force required to rotate the end effectors toward one another, thereby reducing the shear force applied to pivot posts on the arms used to open the jaws. The dual action drive member may be used with a variety of different end effector devices including but not limited to medical grippers, hole punches, dissectors, extractors, scissors, and clamps.

9 Claims, 3 Drawing Sheets

FIG. 5A

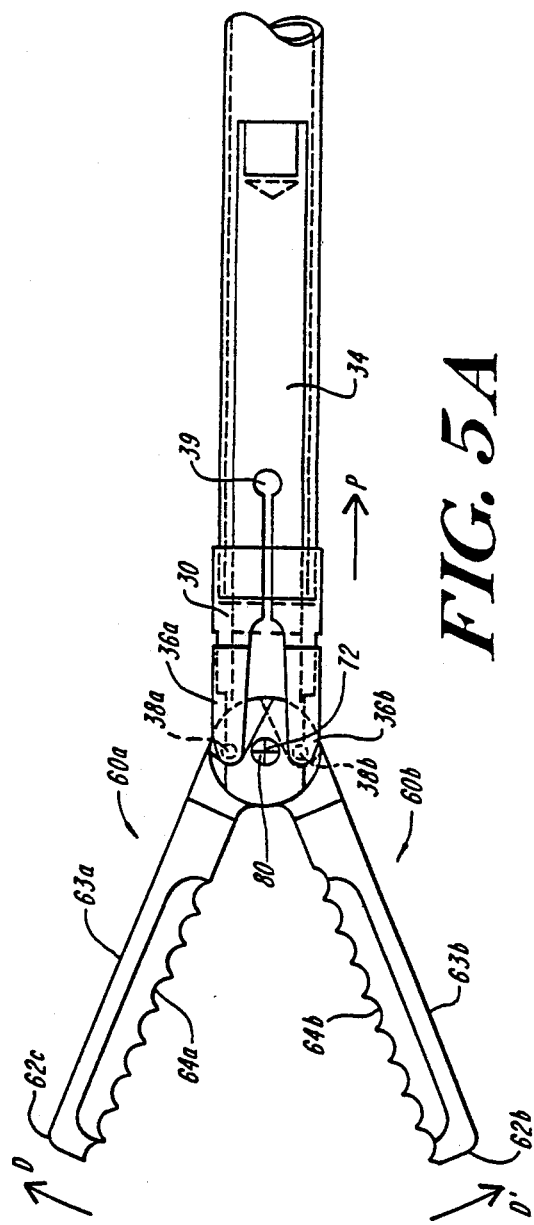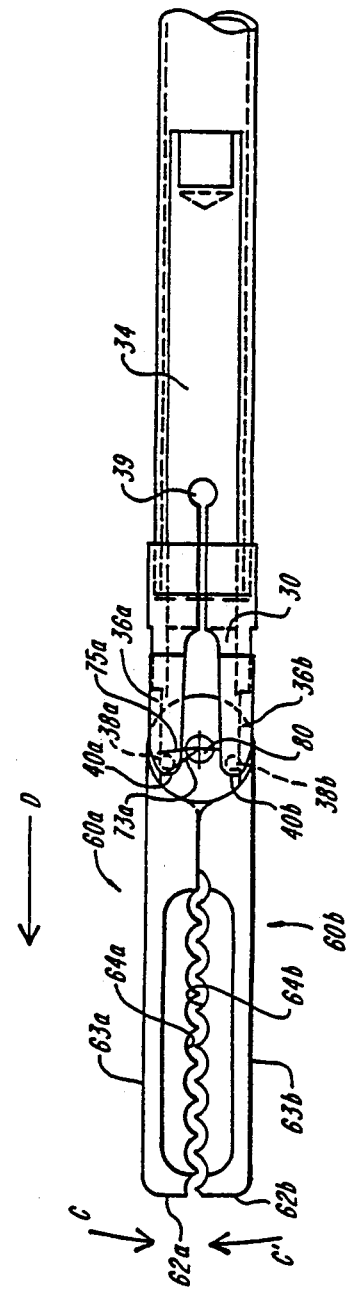

5,263,967

MEDICAL INSTRUMENT WITH DUAL ACTION DRIVE

FIELD OF THE INVENTION

This invention relates to the field of medical instruments, and more particularly to the field of medical instruments having end effectors.

BACKGROUND OF THE INVENTION

For surgical or other procedures, medical tools having end effectors manually manipulated at the end of long extensions are frequently needed. The need particularly arises in arthoscopic and endoscopic surgery. For such procedures, medical devices, such as clamps, scissors and grippers exist in which the end effectors are located at the end of a long extension and are opened and closed by means of opposing handles located at the opposite end of the extension. Typically these devices are relatively small and are used in surgical procedures where a long narrow device provides access to tissue within the body with minimal disturbance of the adjacent tissue.

Referring to FIG. 1, generally these devices 2 have an activation mechanism 4 (only partially depicted) which, attached to articulated arms 6, causes the end effectors to open and close. Also generally these articulated arms are joined together by press-fit pins 8. Pressure applied to close the end effectors may be high enough to shear the pins 8, which then can come free during the procedure, resulting serious complications to the patient.

The present invention relates to a novel dual action drive member which does not apply pressure to close the end effectors of a medical device through pins which can come free and endanger the patient.

SUMMARY OF THE INVENTION

The dual action end effector medical instrument including a dual action drive member disclosed herein uses a dual action drive member to move the end effectors of the instrument, relative to one another, as the dual action drive member is moved proximally or distally within a tubular extension.

In one embodiment, the medical instrument employs two movable end effectors each of which is rotatably attached, by means of a hollow pivot, located substantially adjacent to the proximal end of each end effector, to and within the tubular extension. Each end effector is also attached, between the outer surface of the end effector and the pivot, to a respective arm of the dual action drive member. As the dual action drive member is moved proximally or distally within the tubular extension, the distal ends of the end effectors are made to rotate about the pivot in a direction opposite to one another. The counter rotation of the distal ends of the end effectors opens and closes the instrument. The closing motion involves the application of face to face forces at the ends of the arms of the dual action drive member and thereby avoids the excessive shear forces which occur on the linking pins of the prior art drive members. The dual action drive member may be used with a variety of different end effector devices including but not limited to medical grippers, scissors, punches, extractors, dissectors and clamps.

BRIEF DESCRIPTION OF THE DRAWINGS

Other features and benefits of the invention can be more clearly understood with reference to the specification and the accompanying drawings in which:

FIG. 5 is a plan view of the dual action drive member embodiment of the end effector medical instrument shown in FIG. 2 with the end effectors in the closed configuration; and FIG. 5A is a plan view of the dual action drive member embodiment of the end effector medical instrument shown in FIG. 2 with the end effectors in the open configuration.

DESCRIPTION OF THE PREFERRED EMBODIMENTS

Structure

Figure 1:
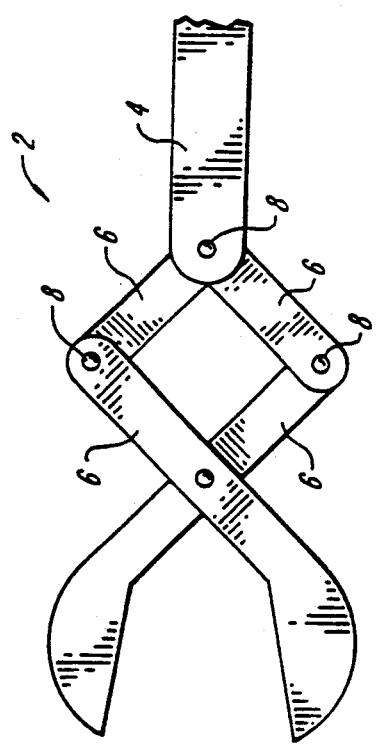
FIG. 1 is a diagram of a dual action drive member used in end effector medical instruments known to the prior art.
Figure 2:
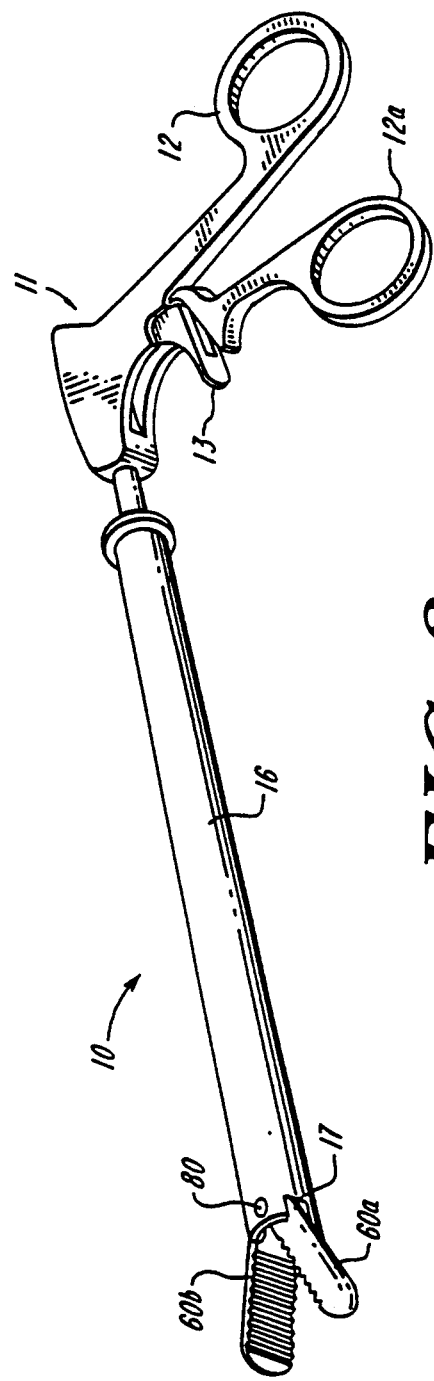
FIG. 2 is a perspective view of an embodiment of a dual action drive member end effector medical instrument of the invention.
Figure 3:
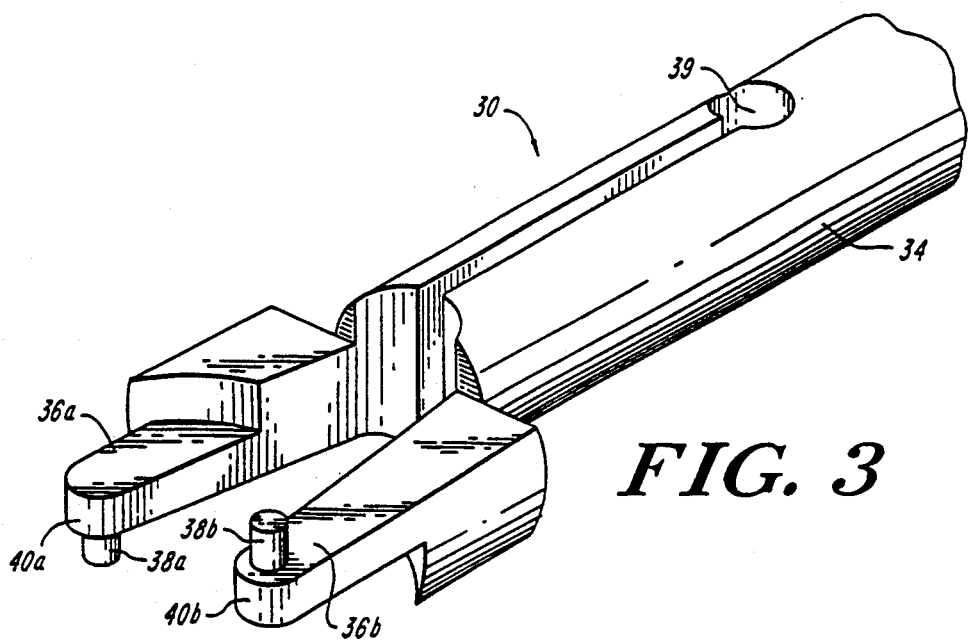
FIG. 3 is a perspective view of an embodiment of the dual action drive member of the end effector medical instrument shown in FIG. 2.
Figure 4:
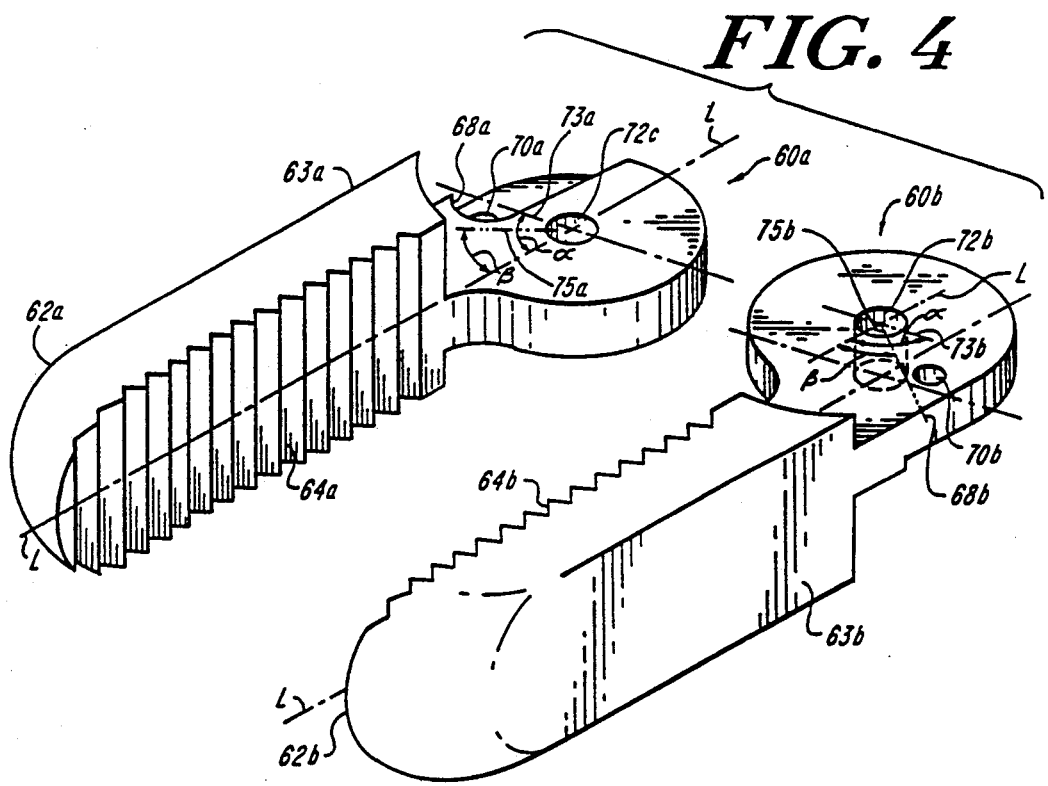
FIG. 4 is a perspective view of an embodiment of a set of end effectors of the embodiment of the end effector medical instrument shown in FIG. 2.

An embodiment of a dual action drive member medical instrument 10 having a dual action drive is shown in FIG. 2. The dual action drive member medical instrument 10 includes a body 14, having a handle portion 11 and a tubular extension 16. Referring also to FIGS. 3 and 4, a dual action drive member 30 and a pair of end effectors 60a, 60b, such as jaws, are positioned within the tubular extension 16. Opposing slots 17 cut into the distal end of the tubular extension 16, permits the end effectors 60a, 60b, to open perpendicularly to the longitudinal axis of the tubular extension 16.

In the embodiment shown, the handle portion 11 includes a fixed leg 12 and a movable leg 12a. The movable leg 12a is movably attached to a drive body 34 (FIG. 3) which is connected to the dual action drive member 30. The motion of the movable leg 12a away from and toward the fixed leg 12 causes the drive body 34 to move distally and proximally, respectively, within the tubular extension 16 so as to open and close, respectively, the end effectors 60a, 60b. Although the embodiment shown opens and closes the end effectors 60a, 60b by the movement of the movable leg 12a away from and toward, respectively, the fixed leg 12, it is contemplated that the movable leg 12a may be movably attached to the drive body 34 such that the motion of the movable leg 12a toward the fixed leg 12 would open the end effectors 60a, 60b. Additionally other activating means, such as triggers, known to one skilled in the art, could be used to move the drive body 34.

It should also be noted that the embodiment shown includes a ratchet 13 which, when engaged, permits the movable leg 12a to be moved only toward the fixed leg 12, thus preventing the end effectors 60a, 60b from releasing an object once it is gripped. By releasing the ratchet 13, the object may be released by moving the movable leg 12a away from the fixed leg 12.

Considering each component separately, the dual action drive member 30 (FIG. 3) includes a pair of arms 36a, 36b joined at their proximal ends in the drive body 34 at a wishbone shaped junction 39. The flexibility provided by the junction 39 permits the end effectors 60a, 60b, to rotate about a central pivot point located between the pair of arms 36a, 36b.

Each arm 36a, 36b includes a retaining post 38a, 38b, respectively, near its distal end. The outside surface 40a, 40b of the distal end of each arm 36a, 36b is in the shape of an arc which engages a complementary shaped relief in its respective end effector 60a, 60b.

The inner surface 64a, 64b of the distal portion of each end effector 60a, 60b (FIG. 4) may be serrated to form a gripping surface or alternatively may include, but not be limited to, scissor blades or clamp tines. The distal portion 62a, 62b, respectively, of each end effector 60a, 60b may be rounded to facilitate the entry of the end effector medical instrument into the region of the medical procedure. In the embodiment shown, the interaction of the inner surfaces 64a, 64b of the two end effectors 60a, 60b firmly retains the object gripped between the gripping surfaces.

A curved relief 68a, 68b proximal to the serrated surface 64a, 64b of each end effector 60a, 60b engages the complementary shaped outside surface 40a, 40b at the distal end of its respective arm 36a, 36b. A pivot hole 72a, 72b respectively, is located near the proximal end of each end effector 60a, 60b, substantially axially aligned with the inner surface 64a, 64b of the respective end effector 60a, 60b. A pivot pin 80 passes through both pivot holes 72a, 72b rotatably anchoring the end effectors 60a, 60b to the tubular extension 16 of the end effector medical instrument 10. The pivot pin 80 acts as the central pivot point for the rotation of the end effectors 60a, 60b. In one embodiment, the pivot pin 80 is hollow. This permits the start of failure to be easily detected before failure of the pivot pin 80 is complete. The pivot pin 80 constrains the end effectors 60a, 60b to remain at their location within the tubular extension 16.

A retaining hole 70a, 70b, located between the outer surface 63a, 63b of each end effector 60a, 60b and the pivot hole 72a, 72b, is engaged by the retaining post 38a, 38b of its respective arm 36a, 36b. As the retaining posts 38a, 38b, of the arms 36a, 36b are moved proximally within the tubular extension 16, the retaining posts 38a, 38b apply a force to their respective retaining holes 70a, 70b. The portions of the end effectors 60a, 60b between the retaining holes 70a, 70b and the pivot holes 72a, 72b respectively act as moment arms 75a, 75b causing the end effector 60a, 60b to rotate about the pivot 80. Conversely, as the outside surfaces 40a, 40b, of the arms 36a, 36b are moved distally within the tubular extension 16, the outside surfaces 40a, 40b apply a force to the curved relief in their respective end effectors 60a, 60b. The portions of the end effectors 60a, 60b between the curved reliefs 68a, 68b and the pivot holes 72a, 72b respectively act as moment arms 73a, 73b causing the end effectors 60a, 60b to rotate about the pivot 80. Thus, during the closing action when the highest force is applied, the retaining posts 38a, 38b are not required to support high shear forces. In the embodiment shown, the moment arms 73a, 73b, are oriented at an acute angle α with respect to the distal part of the longitudinal axis (L) of the end effector 60a, 60b and the moment arms 75a, 75b, are oriented at an acute angle α with respect to the distal part of the longitudinal axis (L) of the end effector 60a, 60b.

Operation

Referring to FIG. 5, when the movable leg 12a of the handle portion 11 moves toward the fixed leg 12, the dual action drive member 30 moves distally (arrow D) within the tubular extension 16. Each arm 36a, 36b of the dual action drive member 30 pushes its respective outside surface 39a, 39b distally within the tubular extension 16. This force, applied by the outside surface 39a, 39b to the respective curved relief 68a, 68b of its respective end effector 60a, 60b (FIG. 4) causes the respective distal end of the end effector 60a, 60b to rotate toward (arrows C,C') the other end effector 60b, 60a thereby bringing the object between the inner surfaces 64a, 64b of the end effectors 60a, 60b.

Conversely, (referring to FIG. 5A), when the movable leg 12a of the handle portion 11 is moved away from the fixed leg 12 the dual action drive member 30 is moved proximally (arrow P) within the tubular extension 16. Each arm 36a, 36b of the dual action drive member 30 pulls its respective retaining post 38a, 38b proximally within the tubular extension 16. Again, because the end effectors 60a, 60b are anchored by pivot pin 80, the force, applied by each retaining post 38a, 38b to its respective retaining hole 70a, 70b (FIG. 4), causes the respective distal end of the end effector 60a, 60b to rotate away (arrows D,D') from the other end effector 60b, 60a thereby opening the end effectors 60a, 60b of the dual action drive end effector medical instrument 10.

Thus the interaction of the end surfaces 40a, 40b of the arms 36a, 36b transfers the force required close the end effectors 60a, 60b without the use of a pinned linkage which can shear during use.

These and other examples of the concept of the invention illustrated above are intended by way of example and the actual scope of the invention is to be determined solely from the following claims.

What is claimed is:

1. A medical instrument comprising:
   a tubular extension having a distal end and a proximal end;
   a first movable end effector pivotally attached by a pivot to said distal end of said tubular extension;
   a second movable end effector pivotally attached by said pivot to said distal end of said tubular extension; and
   a dual action drive member located within the tubular extension and capable of moving between a first proximal position and a second distal position within said tubular extension,
   said dual action drive member comprising a first arm in communication with said first movable end effector and a second arm in communication with said second movable end effector,
   said first arm having a distal end surface for transferring force to said first end effector and said second arm having a distal end surface for transferring force to said second end effector,
   wherein said dual action drive member is capable of moving in a proximal direction to cause said first movable end effector and said second movable end effector to rotate about said pivot away from one another and is capable of moving in a distal direction so as to cause force to be transferred to said first movable end effector by said distal end surface of said first arm and to cause force to be transferred to said second movable end effector by said distal end surface of said second arm thereby to cause said distal end of said second end effector and said distal end of said first end effector to move toward one another.

2. The medical instrument of claim 1 wherein each said end effector is a gripper.

3. The medical instrument of claim 1 wherein each said end effector is a scissor blade.

4. The medical instrument of claim 1 wherein each said end effector is a clamp tine.

5. The medical instrument of claim 1 wherein said extension has a longitudinal axis and comprises a slot in its distal end so as to permit the distal end of said first end effector and the distal end of said second end effector to move in a direction perpendicular to said longitudinal axis of said extension.

6. The medical instrument of claim 1 wherein said first arm and said second arm are joined in a flexible wishbone junction.

7. The medical instrument of claim 1 wherein said pivot is hollow.

8. A medical instrument comprising:
a tubular extension having a distal end, a proximal end and a longitudinal axis;
a handle portion attached adjacent to said proximal end of said tubular extension, said handle portion comprising an activation mechanism;
a first movable end effector pivotally attached by a hollow pivot to said distal end of said tubular extension;
a second movable end effector pivotally attached by said hollow pivot to said distal end of said tubular extension; and
a dual action drive member located within the tubular extension and connected to said activation mechanism, said dual action drive member comprising a first arm and a second arm, said first arm being attached to said first movable end effector and having a distal end surface for transferring force to said first end effector, and said second arm being attached to said second movable end effector and having a distal end surface for transferring force to said second end effector, said first arm and second arm joined in a wishbone junction,
wherein said activation member is capable of moving said dual action drive member between a first proximal position and a second distal position within said tabular extension,
wherein said dual action drive member moving in a distal direction causes said distal end of said first movable end effector and said distal end of said second movable end effector to rotate about said pivot toward one another,
wherein said dual action drive member moving in a proximal direction causes said distal end of said first movable end effector and said distal end of said second movable end effector to rotate about said pivot away from one another, and
wherein said tubular extension comprises a slot in its distal end so as to permit the distal end of said first end effector and the distal end of said second end effector to move in a direction substantially perpendicular to said longitudinal axis of said extension.

9. A medical instrument comprising:
a tubular extension having a longitudinal axis, a distal end and a proximal end;
at least one movable end effector pivotally attached by a pivot to said distal end of said tubular extension; and
a drive member located within the tubular extension and capable of moving between a first proximal position and a second distal position within said tabular extension,
said drive member having at least one arm pivotally attached by a pin and pull to said movable end effector, said arm having a distal end surface for transferring force to said movable end effector,
wherein when said drive member is moved in said distal direction, force is transferred to said movable end effector causing said movable end effector to rotate about said pivot toward said longitudinal axis.

* * * * *

UNITED STATES PATENT AND TRADEMARK OFFICE
CERTIFICATE OF CORRECTION

PATENT NO. : 5,263,967
DATED : November 23, 1993
INVENTOR(S) : William G. Lyons, III It is certified that error appears in the above-indentified patent and that said Letters Patent is hereby corrected as shown below:

Column 3, line 66, "angle $\alpha$ with" should read --angle $\beta$ with--.

Signed and Sealed this

Twenty-seventh Day of December, 1994

Attest:

BRUCE LEHMAN

*Attesting Officer*   *Commissioner of Patents and Trademarks*

Adverse Decisions In Interference

Patent No. 5,263,967, William G. Lyons, III; John Kirwan, MEDICAL INSTRUMENT WITH DUAL ACTION DRIVE, Interference No. 103,917, final judgment adverse to the patentees rendered July 31, 1998, as to claims 1~5.

*(Official Gazette October 27, 1998)*

REEXAMINATION CERTIFICATE (4235th)

United States Patent [19]
Lyons, III et al.

[11] B1 5,263,967
[45] Certificate Issued Dec. 19, 2000

[54] MEDICAL INSTRUMENT WITH DUAL ACTION DRIVE

[75] Inventors: William G. Lyons, III, Wilbraham; John Kirwan, Middleton, both of Mass.

[73] Assignee: Brimfield Precision Incorporated, Brimfield, Mass.

Reexamination Request:
No. 90/003,670, Dec. 23, 1994

Reexamination Certificate for:
Patent No.: 5,263,967
Issued: Nov. 23, 1993
Appl. No.: 07/883,080
Filed: May 15, 1992

Certificate of Correction issued Dec. 27, 1994.

[51] Int. Cl.[7] .......................... A61B 17/28; A61B 17/42; A61B 17/44
[52] U.S. Cl. .......................... 606/205; 606/208; 294/115; 294/116
[58] Field of Search ..................... 606/208, 205, 606/206, 207; 128/751

[56] References Cited

U.S. PATENT DOCUMENTS

| | | | |
|---|---|---|---|
| 2,113,246 | 4/1938 | Wappler | 606/205 |
| 2,518,994 | 8/1950 | Miller | 606/205 |
| 2,704,399 | 3/1955 | Melcher | 606/208 X |
| 3,735,763 | 5/1973 | Shannon et al. | 606/208 |
| 3,964,468 | 6/1976 | Schulz | 128/751 |
| 4,043,343 | 8/1977 | Williams | 606/207 |
| 4,887,612 | 12/1989 | Esser et al. | 128/751 |
| 5,009,661 | 4/1991 | Michelson | 606/205 X |
| 5,052,402 | 10/1991 | Bencini et al. | 606/206 X |
| 5,152,780 | 10/1992 | Honkanen et al. | 606/205 |
| 5,201,759 | 4/1993 | Ferzli | 606/205 X |
| 5,219,357 | 6/1993 | Honkanen et al. | 606/205 |
| 5,366,477 | 11/1994 | Le Marie et al. | 606/208 |
| 5,383,888 | 1/1995 | Zvenyatsky et al. | 606/206 |
| 5,391,180 | 2/1995 | Tovey et al. | 606/205 |

FOREIGN PATENT DOCUMENTS 119405   9/1984   European Pat. Off. .

*Primary Examiner*—Michael H. Thaler

[57] ABSTRACT

A medical instrument including a tubular extension within which and to which two movable end effectors, such as jaw members, are rotatably attached by a pivot. The proximal end of each end effector is pivotally attached to and butts against a drive surface of its respective arm of a dual action drive member also located within the tubular extension. As the dual action drive member is moved proximally or distally within the tubular extension, the distal ends of the end effectors rotate or counter rotate about the pivot in opposition to one another. The dual action drive member paired arms have end surfaces which transfer, to the end effectors, the force required to rotate the end effectors toward one another, thereby reducing the shear force applied to pivot posts on the arms used to open the jaws. The dual action drive member may be used with a variety of different end effector devices including but not limited to medical grippers, hole punches, dissectors, extractors, scissors, and clamps.

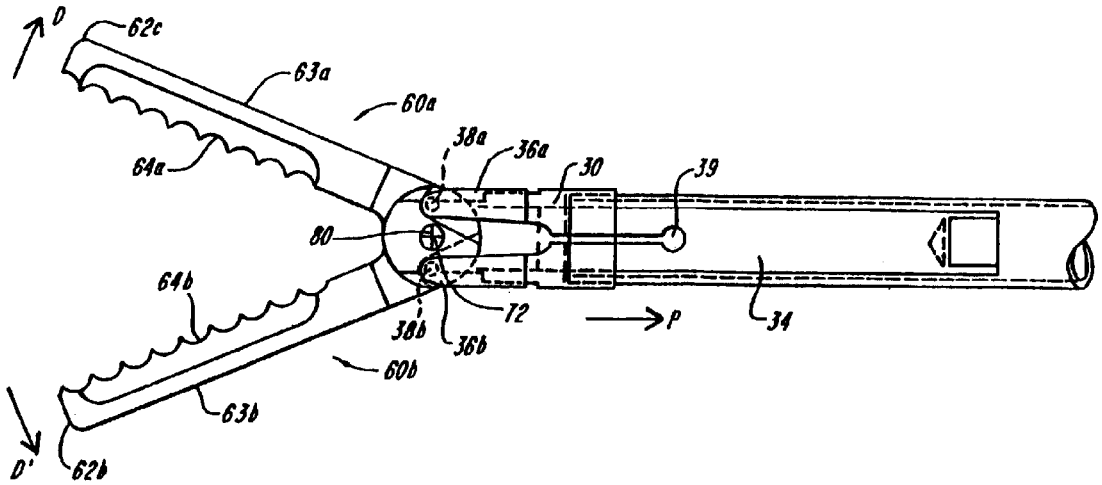

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–5, 7 and 9 are cancelled.

Claims 6 and 8 are determined to be patentable as amended.

6. [The] *A* medical instrument [of claim 1] *comprising:*

*a tubular extension having a distal end and a proximal end;*

*a first movable end effector pivotally attached by a pivot to said distal end of said tubular extension;*

*a second movable end effector pivotally attached by said pivot to said distal end of said tubular extension; and*

*a dual action drive member located within the tubular extension and capable of moving between a first proximal position and a second distal position within said tubular extension,*

*said dual action drive member comprising a first arm in communication with said first movable end effector and a second arm in communication with said second movable end effector,*

*said first arm having a distalmost end surface for transferring force to said first end effector and said second arm having a distalmost end surface for transferring force to said second end effector,* wherein said first arm and said second arm are joined in a flexible wishbone junction *wherein during operation of said medical instrument said arms flex at said wishbone junction; and wherein said dual action drive member is capable of moving in a proximal direction to cause said first movable end effector and said second movable end effector to rotate about said pivot away from one another and is capable of moving in a distal direction so as to cause force to be transferred to said first movable end effector by said distalmost end surface of said first arm and to cause force to be transferred to said second movable end effector by said distal end surface of said second arm thereby to cause said distalmost end of said second end effector and said distal end of said first end effector to move toward one another.*

8. A medical instrument comprising:

a tubular extension having a distal end, a proximal end and a longitudinal axis;

a handle portion attached adjacent to said proximal end of said tubular extension, said handle portion comprising an activation mechanism;

a first movable end effector pivotally attached by a hollow pivot to said distal end of said tubular extension;

a second movable end effector pivotally attached by said hollow pivot to said distal end of said tubular extension; and a dual action drive member located within the tubular extension and connected to said activation mechanism, said dual action drive member comprising a first arm and a second arm, said first arm being attached to said first movable end effector and having a [distal] *distalmost* end surface for transferring force to said first end effector, and said second arm being attached to said second movable end effector and having a [distal] *distalmost* end surface for transferring force to said second end effector, said first arm and said second arm joined in a wishbone junction,

*wherein during operation of said medical instrument said arms flex at said wishbone junction,* wherein said activation member is capable of moving said dual action drive member between a first proximal position and a second distal position within said tubular extension, wherein said dual action drive member moving in a distal direction causes said distal end of said first movable end effector and said distal end of said second movable end effector to rotate about said pivot toward one another, wherein said dual action drive member moving in a proximal direction causes said distal end of said first movable end effector and said distal end of said second movable end effector to rotate about said pivot away from one another, and wherein said tubular extension comprises a slot in its distal end so as to permit the distal end of said first end effector and the distal end of said second end effector to move in a direction substantially perpendicular to said longitudinal axis of said extension.

* * * * *